(12) United States Patent
Komuro (10) Patent No.: US 12,030,301 B2
(45) Date of Patent: Jul. 9, 2024

(54) LIQUID EJECTING DEVICE AND LIQUID EJECTING METHOD

(71) Applicant: SEIKO EPSON CORPORATION, Tokyo (JP)

(72) Inventor: Shintaro Komuro, Matsumoto (JP)

(73) Assignee: Seiko Epson Corporation, Tokyo (JP)

( * ) Notice: Subject to any disclaimer, the term of this patent is extended or adjusted under 35 U.S.C. 154(b) by 178 days.

(21) Appl. No.: 17/659,522

(22) Filed: Apr. 18, 2022

(65) Prior Publication Data
US 2022/0332129 A1  Oct. 20, 2022

(30) Foreign Application Priority Data
Apr. 20, 2021  (JP) ................. 2021-070857

(51) Int. Cl.
*B41J 11/00* (2006.01)
*A61L 2/18* (2006.01)
*B41J 2/005* (2006.01)

(52) U.S. Cl.
CPC ............. *B41J 11/0015* (2013.01); *A61L 2/18* (2013.01); *B41J 2/005* (2013.01); *B41J 2002/0052* (2013.01)

(58) Field of Classification Search
CPC .................. B41J 11/0015; B41J 2/005; B41J 2002/0052; B41J 11/002; A61L 2/18; A61L 2202/15
See application file for complete search history.

(56) References Cited

U.S. PATENT DOCUMENTS 5,578,281 A   11/1996 Kadowaki et al.

FOREIGN PATENT DOCUMENTS

| JP | H03-209595 A | 9/1991 |
|---|---|---|
| JP | 2005-115268 A | 4/2005 |
| JP | 2005115268 A | * 4/2005 |

* cited by examiner

*Primary Examiner* — Bradley W Thies
(74) *Attorney, Agent, or Firm* — WORKMAN NYDEGGER (57) ABSTRACT

A liquid ejecting device includes a first liquid ejecting unit configured to eject recording liquid onto a medium, a second liquid ejecting unit configured to eject disinfectant liquid onto the medium, and a control unit configured to control the first liquid ejecting unit and the second liquid ejecting unit, wherein the control unit is configured to cause the disinfectant liquid to eject avoiding a position at which the recording liquid ejects on the medium.

9 Claims, 11 Drawing Sheets

LIQUID EJECTING DEVICE AND LIQUID EJECTING METHOD

The present application is based on, and claims priority from JP Application Serial Number 2021-070857, filed Apr. 20, 2021, the disclosure of which is hereby incorporated by reference herein in its entirety.

BACKGROUND

1. Technical Field

The present disclosure relates to a liquid ejecting device configured to eject liquid onto a medium and a liquid ejecting method in the liquid ejecting device.

2. Related Art

One example of liquid ejecting devices includes an inkjet printer. The inkjet printer performs recording by ejecting ink that is an example of liquid onto a recording sheet that is an example of media.

In recent years, there is a user need to remove bacteria and viruses adhered to a recording sheet and in connection with such a user need, JP-A-2005-115268 proposes an image forming apparatus configured to perform disinfection processing on a medium. In the image forming apparatus, an ultraviolet lamp or an alcohol application mechanism is provided upstream of a photosensitive drum, and the disinfection processing is performed on the medium before an image is formed on the medium.

When a disinfection processing is performed on the medium using an ultraviolet lamp, it is necessary to temporarily stop the transport of the medium or slow down the transport speed when performing the disinfection processing to obtain a reliable disinfection effect, and thus the printing throughput is readily degraded. Thus, the disinfection by alcohol application is suitable in the perspective of suppressing degradation in the printing throughput.

However, in an inkjet printer configured to perform recording by ejecting ink onto a recording sheet, when an alcohol is applied to the medium prior to image formation, as in the image forming apparatus described in JP-A-2005-115268, ink bleed-through readily occurs, that is, recording quality readily degraded.

SUMMARY

In order to solve the problem described above, a liquid ejecting device according to an aspect of the present disclosure includes a first liquid ejecting unit configured to eject recording liquid onto a medium, a second liquid ejecting unit configured to eject disinfectant liquid onto the medium, and a control unit configured to control the first liquid ejecting unit and the second liquid ejecting unit, wherein the control unit is configured to cause the disinfectant liquid to eject on the medium avoiding a position at which the recording liquid ejects.

Further, a liquid ejecting method according to an aspect of the present disclosure is a liquid ejecting method in a liquid ejecting device, the liquid ejecting device including a first liquid ejecting unit configured to eject recording liquid onto a medium, and a second liquid ejecting unit configured to eject disinfectant liquid onto the medium, wherein the method including causing the disinfectant liquid to eject on the medium avoiding a position at which the recording liquid ejects.

DESCRIPTION OF EXEMPLARY EMBODIMENTS

Hereinafter, the present disclosure will be schematically described.

A liquid ejecting device according to a first aspect includes a first liquid ejecting unit configured to eject recording liquid onto a medium, a second liquid ejecting unit configured to eject disinfectant liquid onto the medium, and a control unit configured to control the first liquid ejecting unit and the second liquid ejecting unit, wherein the control unit is configured to cause the disinfectant liquid to eject on the medium avoiding a position at which the recording liquid ejects.

According to the present aspect, the control unit is configured to cause the disinfectant liquid to eject avoiding the position at which the recording liquid ejects on the medium, and thus degradation in recording quality associated with the disinfectant liquid being ejected can be suppressed.

According to a second aspect, in the first aspect, the control unit is configured to cause the disinfectant liquid to eject at margins along edges on four sides of the medium.

In light of the fact that when a user touches the medium, the user often touches any of four sides of the medium, in the present aspect, the control unit is configured to cause the disinfectant liquid to eject at margins along edges on four sides of the medium, and thus an effective disinfection effect can be achieved while suppressing consumption of the disinfectant liquid. In addition, the disinfectant liquid is ejected to margins along edges on four sides of the medium, and thus almost all the effect of the disinfectant liquid on the recording quality can be eliminated.

According to a third aspect, in the first or second aspect, the second liquid ejecting unit is disposed downstream of the first liquid ejecting unit in a transport direction of the medium.

According to the present aspect, the second liquid ejecting unit is disposed downstream of the first liquid ejecting unit in a transport direction of the medium, and thus a configuration can be obtained to eject the disinfectant liquid after the recording liquid is ejected.

A liquid ejecting device according to a fourth aspect, in the first or second aspect, further includes a head unit that includes the first liquid ejecting unit and the second liquid ejecting unit and configured to move in a width direction that is a direction intersecting the transport direction of the medium, wherein with a first direction being a moving direction when the head unit moves, the second liquid ejecting unit is positioned in a second direction opposite to the first direction with respect to the first liquid ejecting unit.

According to the present aspect, with a first direction being a moving direction when the head unit moves, the second liquid ejecting unit is positioned in a second direction opposite to the first direction with respect to the first liquid ejecting unit, and thus a configuration can be obtained to eject the disinfectant liquid after the recording liquid is ejected.

According to a fifth aspect, in any one of the first to fourth aspects, the first liquid ejecting unit and the second liquid ejecting unit are provided in an identical liquid ejecting head.

According to the present aspect, the first liquid ejecting unit and the second liquid ejecting unit are provided in an identical liquid ejecting head, and thus reduction in the size and the cost of the device can be promoted.

A liquid ejecting device according to a sixth aspect, in any one of the first to fifth aspects, further includes a medium inversion path configured to invert the medium after a first surface of the medium passes through a position facing the first liquid ejecting unit and a position facing the second liquid ejecting unit such that a second surface opposite to the first surface faces the first liquid ejecting unit and the second liquid ejecting unit, wherein the control unit is configured to adjust volume of the disinfectant liquid ejected from the second liquid ejecting unit to reduce a difference between total volume of liquid to be ejected onto the first surface and total volume of liquid to be ejected onto the second surface.

When the difference is increased between the total volume of liquid ejected onto the first surface and the total volume of liquid ejected onto the second surface by the first liquid ejecting unit and the second liquid ejecting unit, there is a risk that curl is generated in the medium and alignment of the media output is degraded.

However, according to the present aspect, the control unit is configured to adjust volume of the disinfectant liquid ejected from the second liquid ejecting unit to reduce a difference between total volume of liquid to be ejected onto the first surface and total volume of liquid to be ejected onto the second surface, and thus curl generated in the medium can be suppressed and degradation in alignment of the media output can be suppressed.

A liquid ejecting device according to a seventh aspect, in any one of the first to sixth aspects, further includes a transporting belt configured to adsorb and transport the medium, the transporting belt being provided at a position facing the first liquid ejecting unit, and a cleaning sheet configured to contact and clean the transporting belt, wherein the control unit includes a cleaning mode in which cleaning of the transporting belt is performed by the cleaning sheet after the disinfectant liquid is ejected from the second liquid ejecting unit onto the transporting belt.

The recording liquid adhered to the transporting belt can be wiped off with the cleaning sheet, however, cleaning effect on particulate matter such as paper dust is weak. When particulate matter such as a paper dust is left on the transporting belt, there is a risk that adsorption between the medium and the transporting belt is degraded the next time the medium is transported and transport accuracy is degraded.

However, according to the present aspect, the control unit includes a cleaning mode in which cleaning of the transporting belt is performed by the cleaning sheet after the disinfectant liquid is ejected from the second liquid ejecting unit onto the transporting belt, and thus particulate matter such as paper dust adhered to the transporting belt can be removed by the cleaning sheet.

A liquid ejecting device according to an eighth aspect, in any one of the first to seventh aspects, further includes a drying section configured to perform drying processing on the medium, the drying section being provided downstream of the first liquid ejecting unit and the second liquid ejecting unit in the transport path of the medium.

A liquid ejecting device according to the present aspect includes a drying section configured to perform drying processing on the medium, the drying section being provided downstream of the first liquid ejecting unit and the second liquid ejecting unit in the transport path of the medium, and thus degradation in alignment of the media output with insufficiently dried condition can be suppressed and can suppress transferring of the liquid between media.

A liquid ejecting method according to a ninth aspect of the present disclosure is a liquid ejecting method in a liquid ejecting device, the liquid ejecting device including a first liquid ejecting unit configured to eject recording liquid onto a medium, and a second liquid ejecting unit configured to eject disinfectant liquid onto the medium, wherein the method including causing the disinfectant liquid to eject on the medium avoiding a position at which the recording liquid ejects.

According to the present aspect, the disinfectant liquid ejects while avoiding the position at which the recording liquid ejects on the medium, and thus degradation in recording quality associated with the disinfectant liquid being ejected can be suppressed.

Hereinafter, the present disclosure will be specifically described.

The X-Y-Z coordinate system illustrated in each drawing is an orthogonal coordinate system, in which the X-axis direction indicates a device depth direction, the Y-axis direction indicates a device width direction, and the Z-axis direction indicates a device height direction.

Figure 1:
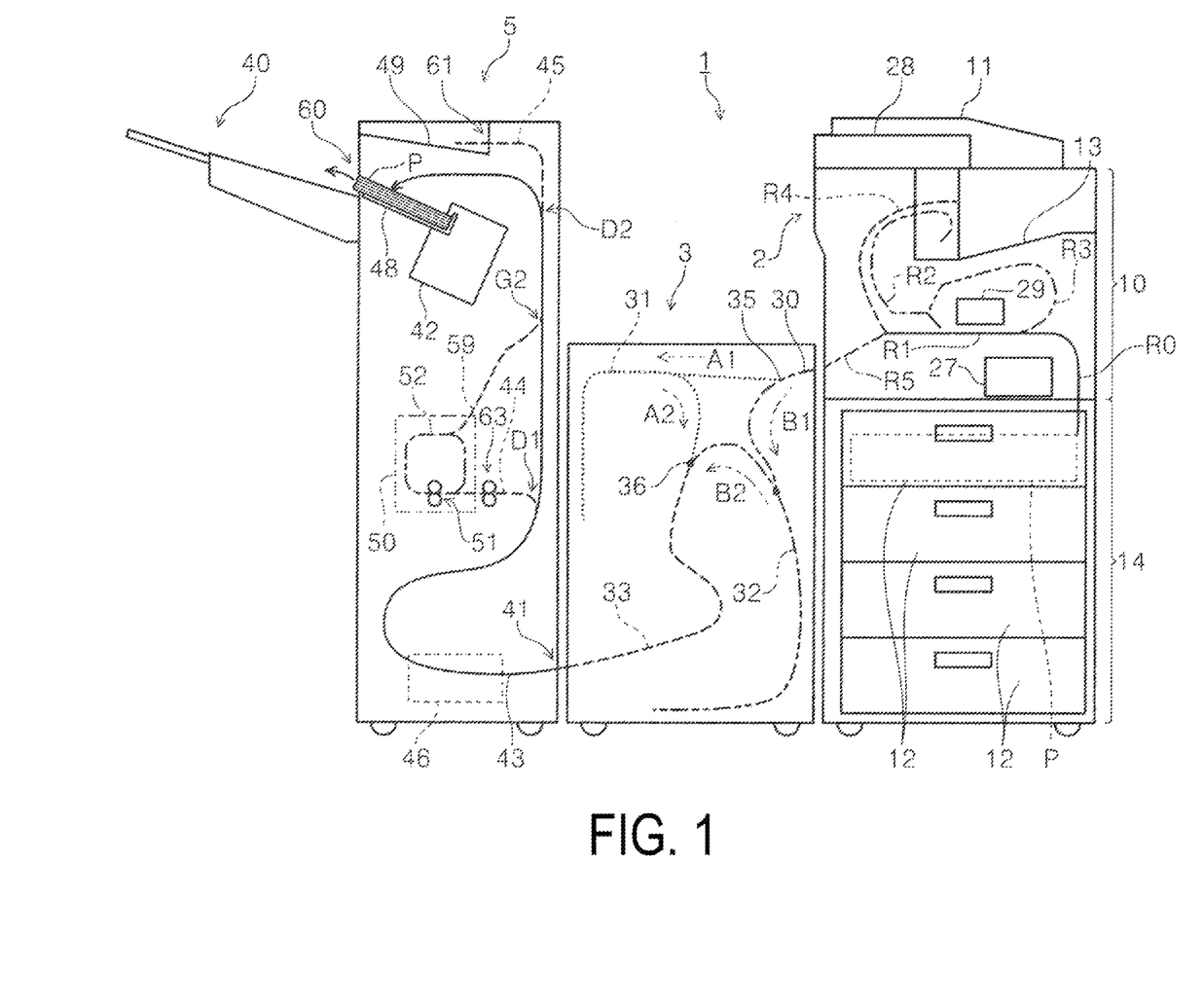
FIG. 1 is a diagram illustrating an overall configuration of a liquid ejecting device.

The liquid ejecting device 1 illustrated in FIG. 1 includes a recording unit 2, an intermediate unit 3, and a post-processing unit 5 from right to left of FIG. 1 in order. Note that, in the liquid ejecting device 1 according to the embodiment, the recording unit 2, the intermediate unit 3, and the post-processing unit 5 are each configured as an independent device and then connected to each other, thereby forming the liquid ejecting device 1. Thus, the liquid ejecting device according to the embodiment may be referred to as a liquid ejecting system or a recording system.

The recording unit 2 is a device configured to perform recording on a medium being transported. The intermediate unit 3 receives the medium after recording from the recording unit 2 and passes the medium to the post-processing unit 5. The recording unit 2 functions to invert the medium and to promote drying of the medium.

The post-processing unit 5 is provided with a punching mechanism section 46 configured to perform punching processing on the medium, a drying section 50 configured to perform drying processing on the medium, and an edge binding section 42 configured to perform edge binding processing in which the media is bundled to bind edges of the media.

Hereinafter, the recording unit 2, the intermediate unit 3, and the post-processing unit 5 are described in detail in order.

The recording unit 2 is configured as a multifunction machine including a printer section 10 configured to perform recording on a medium and a scanner section 11 that is an example of image capturing devices. In the embodiment, the printer section 10 is configured as a so-called inkjet type printer configured to eject ink, which is an example of recording liquid, onto a medium to perform recording.

A cassette accommodation section 14 including a plurality of medium accommodation cassettes 12 is provided in a lower part of the printer section 10. A medium P accommodated in the medium accommodation cassette 12 is fed to a recording transport path R1 through a feeding path R0 and onto which recording is performed by a recording section 29 described below. The medium after recording by the recording section 29 is fed to a switchback path R2 when double-sided recording is performed, then fed to an inversion path R3, and again fed to the recording transport path R1. The medium on which recording is performed only on a first surface or the medium on which recording is performed on both the first surface and a second surface is fed to either a face-down output path R4 or a face-up output path R5. The medium fed to the face-down output path R4 is output to a post-recording output tray 13 provided above the recording section 29. The medium fed to the face-up output path R5 is passed to the intermediate unit 3.

As described above, the printer section 10 has a medium inversion path to invert the medium after the first surface of the medium passes through a position facing the recording section 29 such that the second surface opposite to the first surface faces the recording section 29. The medium inversion path includes the switchback path R2 and the inversion path R3 in the embodiment.

Figure 2:
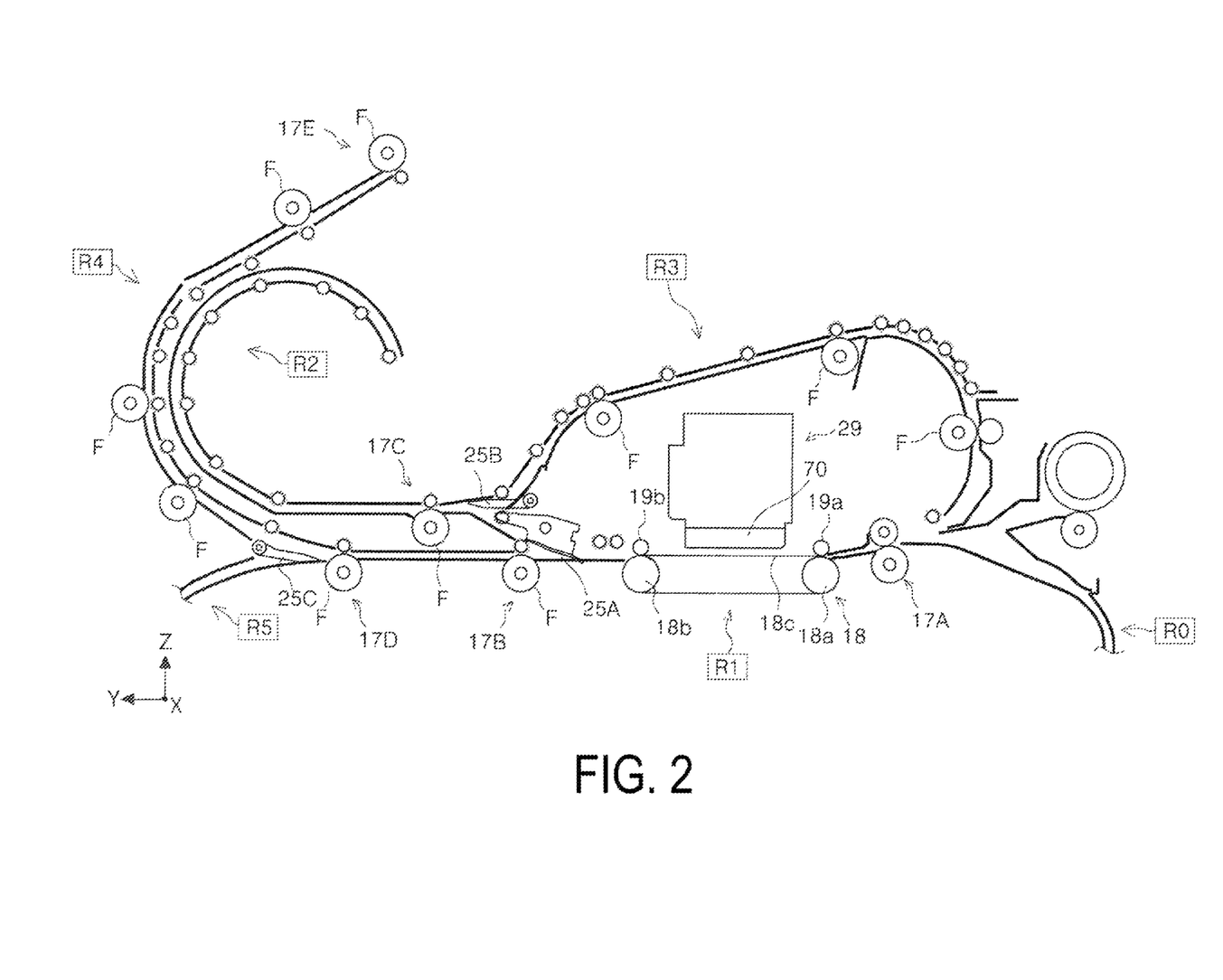
FIG. 2 is a diagram illustrating a medium transport path in a printer section.

Referring now to FIG. 2, the medium transport path of the printer section 10 will be further described. Note that rollers indicated by the reference sign F in FIG. 2 are rollers configured to rotate by receiving power of a motor (not illustrated), and the other rollers without any sign are driven rollers most of which are spurs including an outer circumferential surface having teeth.

The feeding path R0 is a path to a transport roller pair 17A. The recording transport path R1 is a linear path from the transport roller pair 17A to a transport roller pair 17B. The switchback path R2 is a path formed in a curled shape from a transport roller pair 17C in the +Y direction. The inversion path R3 is a curved path running above the recording section 29 from the transport roller pair 17C to the recording roller pair 17A. The face-down output path R4 is a path extending from the transport roller pair 17B in the +Y direction and curving to a transport roller pair 17E. The face-up output path R5 is an obliquely downward path from a transport roller pair 17D.

In the recording transport path R1, a recording sheet receives feeding force from the transport roller pair 17A and a belt unit 18 and is fed in the +Y direction. The belt unit 18 includes a transporting belt 18c. The transporting belt 18c is an endless belt formed from a base material made from urethane, rubber, or the like in which a conductive material is included as necessary to adjust a resistance value, the transporting belt 18c being looped around a drive pulley 18a upstream thereof and a driven pulley 18b downstream thereof and being applied a predetermined tension by a tensioner (not illustrated).

The drive pulley 18a is rotationally driven by a motor (not illustrated). When the drive pulley 18a is rotationally driven, the transporting belt 18c circles around the drive pulley 18a and the driven pulley 18b, thereby the recording sheet adsorbed to the transporting belt 18c is transported.

A charge roller (not illustrated) is in contact with the transporting belt 18c and is rotationally driven in response to circling operation of the transporting belt 18c. A power supply (not illustrated) configured to apply DC voltage to the charge roller is coupled to the charge roller and the charge roller supplies an electrical charge to a site in contact with the transporting belt 18c, and thus the recording sheet is electrostatically adsorbed to the transporting belt 18c.

Figure 3:
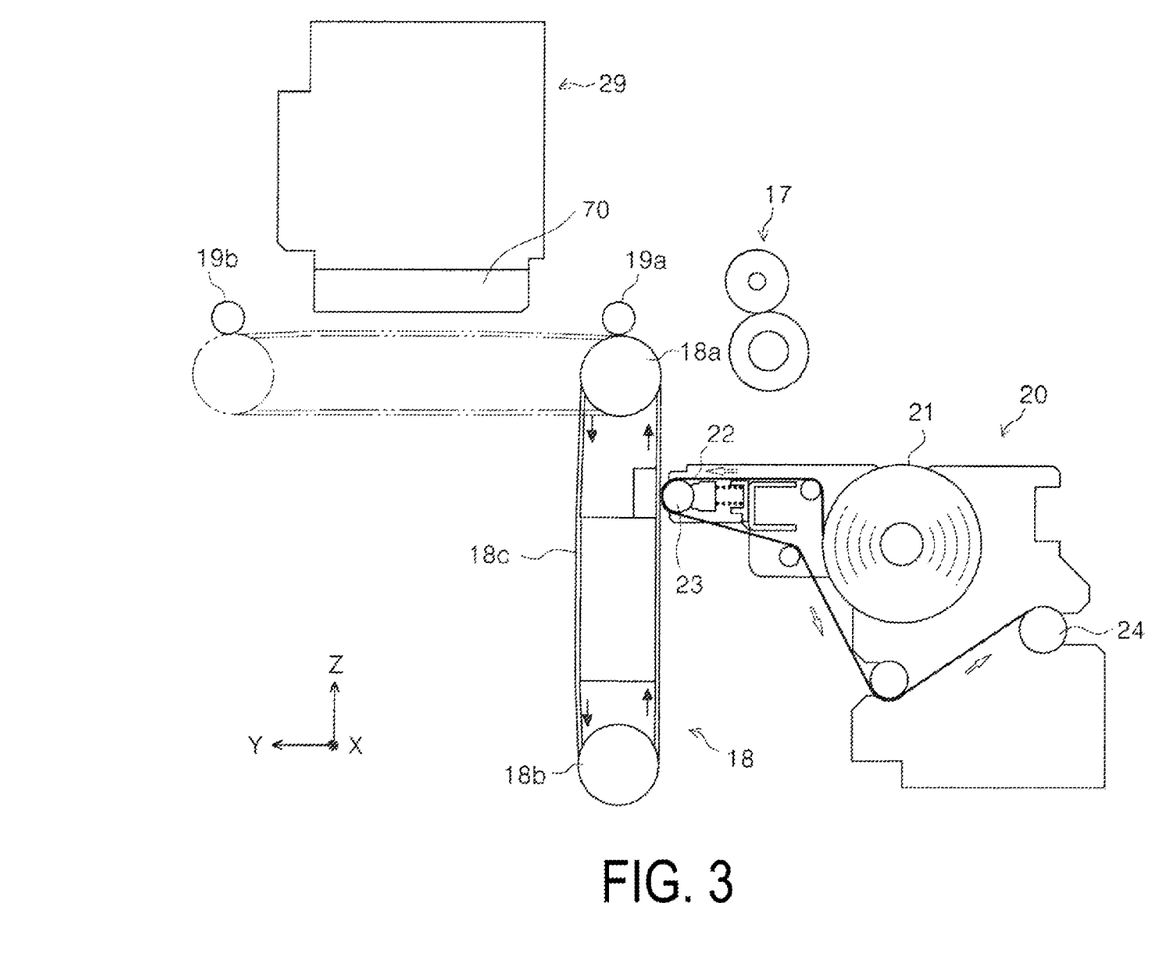
FIG. 3 is a diagram illustrating a configuration of cleaning a transporting belt by a cleaning sheet.

Referring now to FIG. 3, a cleaning unit 20 configured to clean the transporting belt 18c will be described.

The belt unit 18 can switch between a state indicated by a two-dot chain line in FIG. 3, or a recording state, and a state indicated by a solid line, or a cleaning state. In other words, the belt unit 18 is provided such that the bely unit 18 can rotate about an axial center of the drive pulley 18a and switches between the recording state and the cleaning state by rotating.

A cleaning unit 20 is provided at a position facing the belt unit 18 that is switched to the cleaning state. The cleaning unit 20 includes a sheet roll 21 formed by winding a cleaning sheet 22, a take-up roll 24, and a pressing roller 23. The cleaning sheet 22 is unwound from the seat roll 21 by rotation of the take-up roll 24 driven by a motor (not illustrated). Open arrows illustrated in FIG. 3 indicate a movement direction of the cleaning sheet 22 when cleaning and black marking arrows indicate a movement direction of the transporting belt 18c when cleaning.

In the embodiment, the cleaning sheet 22 is a fabric. However, the cleaning sheet 22 is not limited to a fabric and may be any sheet as long as it can clean a surface of the transporting belt 18c. For example, a felt, a non-woven fabric, or the like may be used. The pressing roller 23 is pressed against the belt unit 18 by a spring and the cleaning sheet 22 is pressed against the transporting belt 18c by the pressing roller 23, and thus the transporting belt 18c is cleaned.

Referring back to FIG. 2, a flap 25A is provided downstream of the belt unit 18 and the flap 25A switches the transport direction of the medium to either an obliquely upward direction or a straight direction. When the transport direction of the medium is directed to the obliquely upward direction by the flap 25A, the medium enters the switchback path R2. A flap 25B is provided at or near an inlet of the switchback path R2 and the medium is guided to the inversion path R3 by the flap 25B when the medium is directed from the switchback path R2 toward the inversion path R3.

Further, a flap 25C is provided in the vicinity of the transport roller pair 17D the flap 25C switches the transport destination of the medium to either the face-down output path R4 or the face-up output path R5.

Referring back to FIG. 1, the recording unit 2 is provided with a control unit 27 configured to control various operations in the recording unit 2. Note that the liquid ejecting device 1 is configured such that the recording unit 2, the intermediate unit 3, and the post-processing unit 5 are mechanically and electrically coupled to each other to be able to transport the medium from the recording unit 2 to the post-processing unit 5 and the control unit 27 can control various operations in the intermediate unit 3 and the post-processing unit 5 in addition to the recording unit 2.

The recording unit 2 includes an operation section 28 and is configured to be able to input various configurations and execution commands related to various processing in the recording unit 2, the intermediate unit 3, and the post-processing unit 5 from the operation section 28. Also, the operation section 28 includes a display panel (not illustrated) and is configured to be able to display various types of information on the display panel.

Note that when an external computer (not illustrated) is coupled to the liquid ejecting device 1, the external computer can perform various configurations and execution commands that are similar to various configurations and execution commands performed by the operation section 28.

Next, the intermediate unit 3 will be described. The intermediate unit 3 illustrated in FIG. 1 passes the medium received from the recording unit 2 to the post-processing unit 5. The intermediate unit 3 is disposed between the recording unit 2 and the post-processing unit 5. The medium transported on the face-up output path R5 of the recording unit 2 is received by the intermediate unit 3 via a receiving path 30 and transported toward the post-processing unit 5.

In the intermediate unit 3, there are two transport paths configured to transport the medium. The first transport path is a path from the receiving path 30 to a merged path 33 via a first switchback path 31 indicated by a dashed line in FIG. 1. The second path is a path from the receiving path 30 to the merged path 33 via a second switchback path 32 indicated by a two-dot chain line in FIG. 1.

The first switchback path 31 is a path configured to receive the medium in the direction of the arrow A1 and subsequently causes the medium to switchback in the direction of the arrow A2. The second switchback path 32 is a path configured to receive the medium in the direction of the arrow B1 and subsequently causes the medium to switchback in the direction of the arrow B2.

The receiving path 30 branches into the first switchback path 31 and the second switchback path 32 at a branching section 35. The branching section 35 is provided with a flap (not illustrated) configured to switch the destination of the medium to either the first switchback path 31 or the second switchback path 32.

Further, the first switchback path 31 and the second switchback path 32 are merged at a merging section 36. Thus, whether the medium is sent from the receiving path 30 to the first switchback path 31 or the second switchback path 32, the medium can be passed to the post-processing unit 5 via the common merged path 33.

The intermediate unit 3 receives the medium from the recording unit 2 into the receiving path 30 with the most recent recording surface facing up, however, the medium is curved and inverted at the merged path 33 to be the most recent recording surface facing down.

Thus, the medium with the most recent recording surface facing down is passed from the +Y direction of the intermediate unit 3 to a first transport path 43 of the post-processing unit 5.

Note that the receiving path 30, the first switchback path 31, the second switchback path 32, and the merged path 33 are each provided with one or more roller pairs (not illustrated) as an example of a unit that transports a medium.

When recording is performed continuously on a plurality of media in the recording unit 2, the media that entered the intermediate unit 3 are alternately fed to a transport path passing through the first switchback path 31 and a transport path passing through the second switchback path 32. This enables the throughput of medium transport in the intermediate unit 3 to be improved.

Further, in a configuration in which recording is performed by ejecting ink onto a medium, as the recording unit 2 according to the embodiment, in a case where the medium is wet when processing is performed on the post-processing unit 5 and a second unit 6 in the subsequent stage, the recording surface may be rubbed off and the alignment of the medium may be poor.

Passing the medium after recording from the recording unit 2 to the post-processing unit 5 via the intermediate unit 3 allows the transport time until the medium after recording is fed to the post-processing unit 5 to be increased and the medium to be further dried before reaching the post-processing unit 5 or the second unit 6.

Next, the post-processing unit 5 will be described. The post-processing unit 5 illustrated in FIG. 1 includes a receiving section 41 configured to receive a medium from the intermediate unit 3 down below in the −Y direction. The medium transported on the merged path 33 of the intermediate unit 3 enters the post-processing unit 5 from the receiving section 41 and is passed to the first transport path 43.

The post-processing unit 5 includes a drying section 50 configured to perform drying processing on a medium received from the receiving section 41, and an edge binding section 42 configured to perform processing on the medium received from the receiving section 41 or the medium processed in the drying section 50.

The post-processing unit 5 includes a first transport path 43 configured to transport a medium received from the receiving section 41, and a second transport path 44 that branches off from the first transport path 43 at a first branching section D1 and configured to feed the medium to the drying section 50. The first branching section D1 is provided with a flap (not illustrated) configured to switch the destination of the medium between the first transport path 43 and the second transport path 44.

The edge binding section 42 is a component configured to perform edge binding processing that binds edges of media, such as, for example, a corner portion on one side of the media or an edge one side of the media. The edge binding section 42 includes a stapler as an example.

The drying section 50 is a component configured to perform drying processing on the medium. In the embodiment, the drying section 50 dries the medium by heating the medium.

More specifically, the drying section 50 includes a heat roller pair 51 as a drying processing section configured to perform drying processing of the medium and a loop transport path 52 that is capable of circling transporting of the medium. The second transport path 44 branched off from the first transport path 43 is merged into the loop transport path 52 upstream of the heat roller pair 51 and the medium can be fed by a transport roller pair 63 provided in the second transport path 44 and introduced into the loop transport path 52.

The heat roller pair 51 in the embodiment has a lower roller which is a drying driving roller that is driven by a drive source (not illustrated) and an upper roller which is a drying driven roller that is rotationally driven by the rotation of the drying driving roller. The drying driving roller is heated by a heater (not illustrated), thereby the drying driving roller generates heat to perform drying of the medium.

Note that the medium fed from the intermediate unit 3 enters, with the most recent recording surface facing down, the second transport path 44 via the first transport path 43 from the receiving section 41 of the post-processing unit 5. The medium is then nipped into the heat roller pair 51 with the most recent recording surface facing down. Thus, in the heat roller pair 51, a roller to be heated is a roller configured to contact the most recent recording surface of the medium.

The drying section is provided with a loop transport path 52 and is configured to be capable of circling transporting of the medium at the loop transport path 52, and thus the drying processing by the heat roller pair 51 can be performed multiple times by circling transporting the medium multiple times. Thus, the medium can be dried more reliably.

The medium after drying by the drying section 50 is fed to a fourth transport path 59 coupled to the loop transport path 52 and merged into the first transport path 43 at a second merging section G2.

The post-processing unit 5 also includes a punching mechanism section 46 configured to perform punching processing on a medium received from the receiving section 41. The punching mechanism section 46 is provided at a position at or near the receiving section 41 on the first transport path 43 through which the medium received in the post-processing unit 5 passes and is configured to be able to perform the punching processing upstream of the first transport path 43.

The medium received from the receiving section 41 can be fed to a processing tray 48. In the processing tray 48, the medium is stacked on the processing tray 48 with a trailing edge in the transport direction aligned. When a predetermined number of media P is stacked on the processing tray 48, edge binding processing by the edge binding section 42 can be performed on the trailing edges of the media P.

The medium processed by the edge binding section 42 is output from a first output section 60 to the outside of the device of the post-processing unit 5 by a unit configured to perform outputting (not illustrated) and is placed on a first tray 40.

Further, a third transport path 45 that branches off from the first transport path 43 at a second branching section D2 downstream of the first branching section D1 is coupled to the first transport path 43. A flap (not illustrated) configured to switch the destination of the medium between the first transport path 43 and the third transport path 45 is provided at the second branching section D2.

An upper tray 49 is provided on an upper portion of the post-processing unit 5. The third transport path 45 continues from the second branching section D2 to a second output section 61 and the medium transported on the third transport path 45 is output from the second output section 61 to the upper tray 49. That is, the medium received from the receiving section 41 can be output to the upper tray 49 without passing through the edge binding section 42.

Next, ejection of the disinfecting liquid onto the medium in the recording unit 2 will be described. In the liquid ejecting device 1, the recording section 29 included in the recording unit 2 is configured to be capable of ejecting disinfectant liquid onto the medium. Hereinafter, the disinfectant liquid is referred to as a disinfecting liquid. Although various types of disinfecting liquid are applicable to the disinfecting liquid according to aspects of the present disclosure, liquid in which a percent concentration of ethanol by volume is in a range from 70% to 90% by volume is used as an example. The ethanol concentration can be changed as appropriate in the range described above or outside the range depending on the intended disinfection effect.

Note that the disinfection shall be used herein in the sense of reducing at least any of bacteria and viruses.

Figure 4:
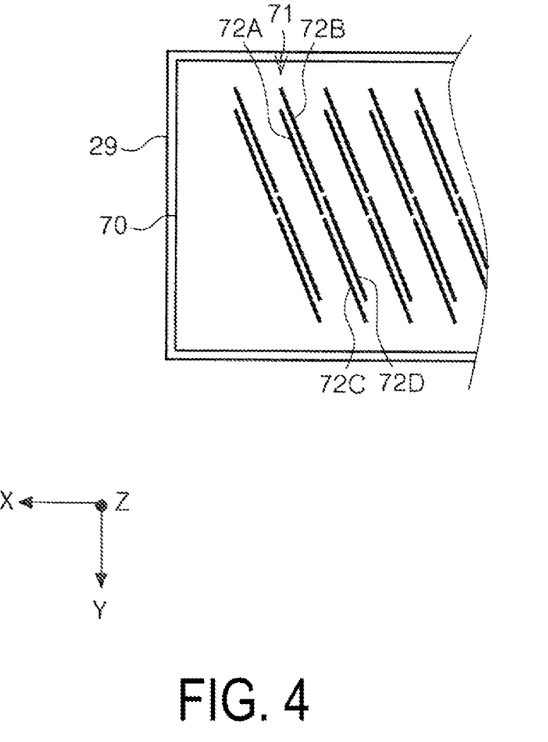
FIG. 4 is a diagram illustrating nozzle rows provided in a liquid ejecting head.

FIG. 4 illustrates nozzle rows provided in a liquid ejecting head 70 included in the recording section 29. The liquid ejecting head 70 according to the embodiment is a liquid ejecting head provided such that nozzle groups 71 extending in the Y-axis direction cover throughout a sheet width along the X-axis direction, and is configured as a liquid ejecting head capable of recording throughout the sheet width without moving in the X-axis direction, or a sheet width direction. Note that the liquid ejecting head 70 is supplied with ink and disinfecting liquid by an ink tube (not illustrated) from a liquid accommodation section (not illustrated). The liquid accommodation section can be refilled with ink and disinfecting liquid.

To be strict, a nozzle group 71 extends in a direction intersecting both the X-axis direction and the Y-axis direction and includes four nozzle rows of nozzle rows 72A, 72B, 72C, and 72D. Although each nozzle row is formed from a plurality of ink ejecting nozzles, each nozzle row is illustrated in a straight line for convenience of illustration.

In the embodiment, the nozzle rows 72A, 72B, and 72D of the nozzle group 71 are used as ink ejecting nozzles. That is, the nozzle rows 72A, 72B, and 72D form a first liquid ejecting unit configured to eject recording ink. The ink ejected from the nozzle rows 72A, 72B, and 72D is pigment ink of black (BK) as an example. However, the ink is not limited to pigment ink and the ink may be black (BK) dye ink.

The nozzle row 72C is then used as a nozzle configured to eject the disinfecting liquid. In other words, the nozzle row 72C forms a second liquid ejecting unit configured to eject disinfectant liquid. In this manner, the first liquid ejecting unit, or the nozzle rows 72A, 72B, and 72D, and the second liquid ejecting unit, or the nozzle row 72C, are provided in the identical liquid ejecting head 70, and thus reduction in the size and the cost of the device can be promoted.

The nozzle row 72C is positioned downstream of the nozzle rows 72A and 72B in the +Y direction, or the sheet transport direction. In addition, the nozzle row 72C and the nozzle row 72D have, when the nozzle row 72C and the nozzle row 72D are at an identical position in the X-axis direction, a relationship in which an ink ejecting nozzle of the nozzle row 72C is positioned downstream of an ink ejecting nozzle of the nozzle row 72D in the +Y direction, or the sheet transport direction.

Note that, in addition to the nozzle row 72C, the nozzle row 72D may be used as a nozzle configured to eject the disinfecting liquid. In this case, the nozzle rows 72A and 72B are ink ejecting nozzles.

The liquid ejecting head 70 included in the recording section 29 is configured as described above, and thus the disinfecting liquid can be ejected onto the medium, thereby the disinfection of the medium can be performed.

Here, in a relationship between a position where the ink ejects on the medium and a position where the disinfecting liquid ejects on the medium, the control unit 27 is configured to eject the disinfecting liquid to avoid an ink ejecting position.

Figure 7:
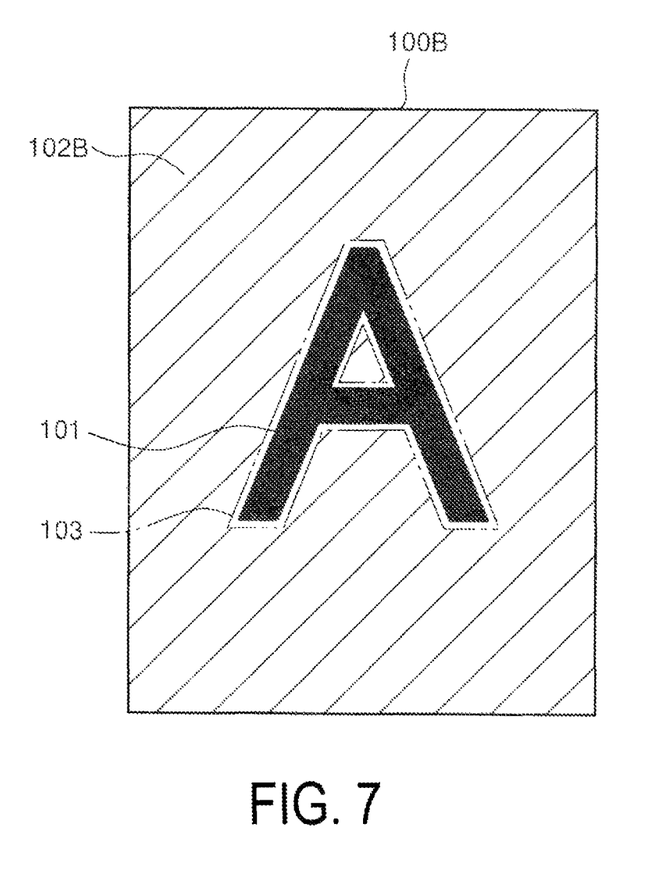
FIG. 7 is a diagram illustrating an example of an ink ejecting region and a disinfecting liquid ejecting region on a recording sheet.

FIG. 7 illustrates an example of ejecting the disinfecting liquid while avoiding the ink ejecting position and a recording region 101 is formed on a medium 100B by ejection of ink. The two-dot chain line indicated by the reference sign 103 is not a line formed on the medium and is a virtual line for indicating an edge of a region to eject the disinfecting liquid. The two-dot chain line 103 is along the edge of the recording region 101 and is an edge of a disinfecting liquid ejecting region 102B. Note that, in addition to the case where the two-dot chain line 103 is identical to the edge of the recording region 101, the two-dot chain line 103 may be configured to have a predetermined distance with respect to the edge of the recording region 101.

In this manner, the control unit 27 is configured to eject the disinfecting liquid while avoiding the ink ejecting position. In other words, a liquid ejecting method in the liquid ejecting device 1 includes a method of ejecting the disinfecting liquid while avoiding the ink ejecting position. Thus, degradation in recording quality associated with ejecting disinfecting liquid can be suppressed. In addition, in the example, the disinfecting liquid is ejected onto most regions except the ink ejecting position, and thus good disinfection effect can be achieved.

Figure 8:
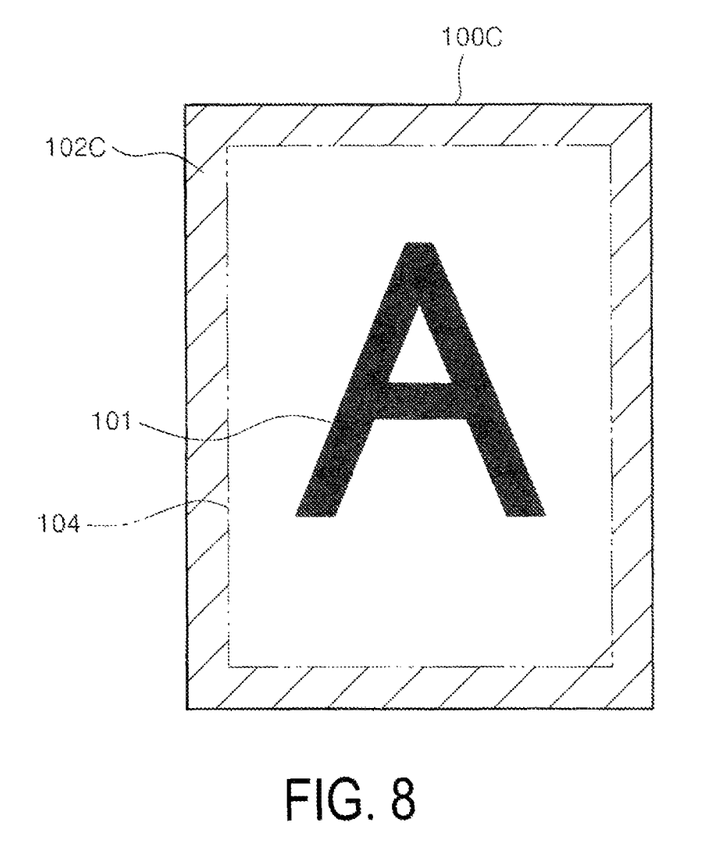
FIG. 8 is a diagram illustrating another example of an ink ejecting region and a disinfecting liquid ejecting region on a recording sheet.

Next, FIG. 8 illustrates another example of ejecting the disinfecting liquid while avoiding the ink ejecting position and the recording region 101 is formed on a medium 100C by ejection of ink. The two-dot chain line indicated by the reference sign 104 is not a line formed on the medium and is a virtual line for indicating an edge of a region to eject the disinfecting liquid. The two-dot chain line 104 is along the four sides of the medium 100C and is an edge of a disinfecting liquid ejecting region 102C.

In this case as well, the control unit 27 is configured to eject the disinfecting liquid while avoiding the ink ejecting position, and thus degradation in recording quality associated with ejecting disinfecting liquid can be suppressed. Also, in the example, the control unit 27 is configured to cause the disinfecting liquid to eject at margins along edges on four sides of the medium, that is, in a region where the user is prone to touch, and thus a disinfection effect is effectively achieved while suppressing consumption of disinfecting liquid. In addition, almost all the effect of disinfecting liquid on recording quality can be eliminated.

Additionally, as described with reference to FIG. 4, in the sheet transport direction, the second liquid ejecting unit, or the nozzle row 72C configured to eject the disinfecting liquid, is positioned downstream of the first liquid ejecting unit, or the nozzle rows 72A, 72B, and 72D, in the +Y direction or in the sheet transport direction, and thus a configuration can be obtained to eject the disinfecting liquid after the recording liquid is ejected. Note that in a case where the disinfecting liquid is to eject while avoiding the ink ejecting position, the nozzle row configured to eject the disinfecting liquid may be upstream of the nozzle row configured to eject the ink, or may be at an identical position to the nozzle row configured to eject the ink in the sheet transport direction.

Figure 9:
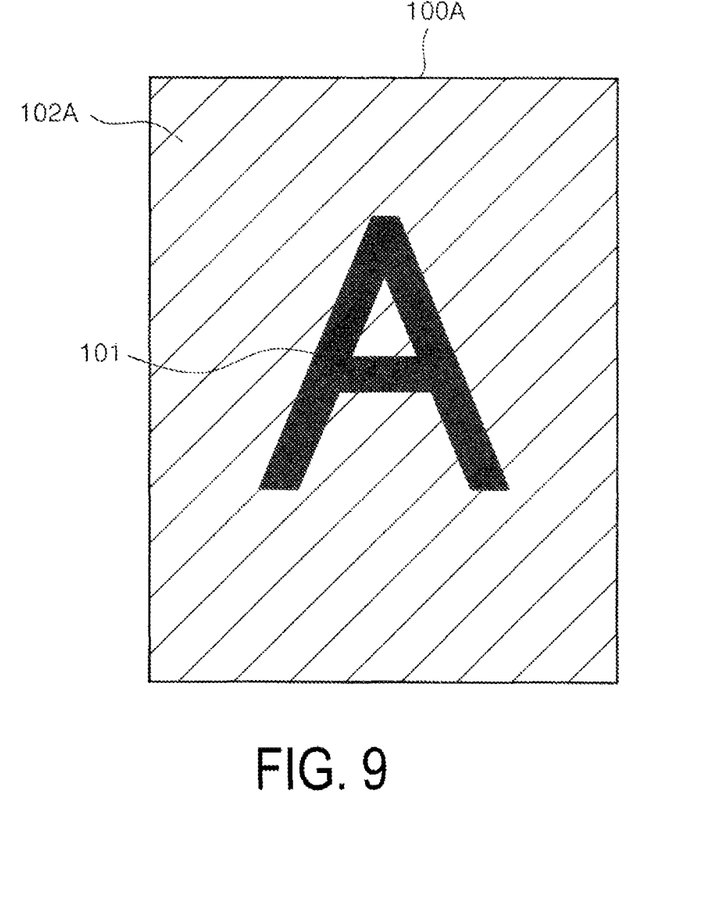
FIG. 9 is a diagram illustrating yet another example of an ink ejecting region and a disinfecting liquid ejecting region on a recording sheet.

Note that in a case where the disinfecting liquid is to eject on the ink ejecting position, the disinfecting liquid may eject after the ink is ejected. FIG. 9 illustrates an example of ejecting the disinfecting liquid at the ink ejecting position and a recording region 101 is formed on a medium 100A by ejection of ink. A region 102A indicated by hatching in FIG. 9 is a disinfecting liquid ejecting region in which the disinfecting liquid is ejected, and the disinfecting liquid ejecting region 102A includes the recording region 101 and is configured to cover throughout the medium. Thus, the disinfecting liquid also ejects at a position where the ink ejects on the medium 100A.

Here, the control unit 27 (see FIG. 1) controls the liquid ejecting head 70 such that the disinfecting liquid ejects after the ink is ejected at a position where the ink ejects on the medium. As a result, in comparison to the case where the ink is ejected onto the medium in a wet state due to the disinfecting liquid, the ink bleed-through can be suppressed, that is, degradation in recording quality can be suppressed.

In addition, the ink is pigment ink in the example, and thus the ink bleed-through can be suppressed even when the disinfecting liquid ejects after the ink is ejected.

Figure 5:
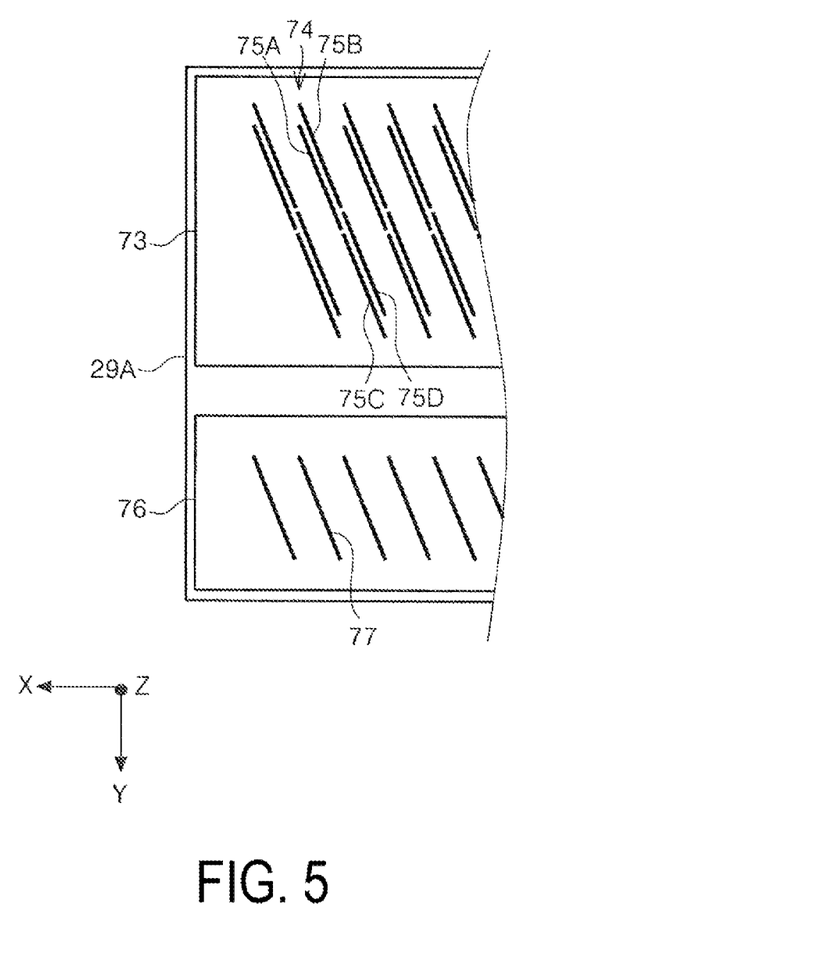
FIG. 5 is a diagram illustrating another embodiment of nozzle rows provided in a liquid ejecting head.

Next, the liquid ejecting head can be configured as illustrated in FIG. 5. A recording section 29A illustrated in FIG. 5 is a variation of the recording section 29 described above. The recording section 29A includes an upstream liquid ejecting head 73. The upstream liquid ejecting head 73 is a liquid ejecting head provided, similar to the liquid ejecting head 70 illustrated in FIG. 4, such that nozzle groups 74 extending in the Y-axis direction cover throughout a sheet width along the X-axis direction, and is configured as a liquid ejecting head capable of recording throughout the sheet width without moving in the X-axis direction, or a sheet width direction.

To be strict, the nozzle group 74 extends in a direction intersecting both the X-axis direction and the Y-axis direction and includes four nozzle rows of nozzle rows 75A, 75B, 75C, and 75D.

In the embodiment, all the nozzle rows 75A, 75B, 75C, and 75D included in the nozzle group 74 are used as ink ejecting nozzles. That is, the nozzle rows 75A, 75B, 75C, and 75D form a first liquid ejecting unit configured to eject recording ink. The ink ejected from the nozzle rows 75A, 75B, 75C, and 75D are, as an example, pigment ink of cyan (C), magenta (M), yellow (Y), and black (K), respectively. However, the ink is not limited to pigment ink and may be dye ink.

Also, in the recording section 29A, a downstream liquid ejecting head 76 is provided downstream of the upstream liquid ejecting head 73 in the +Y direction, or the sheet transport direction. The downstream liquid ejecting head 76 is provided such that nozzle rows 77 extending in the Y-axis direction cover throughout the sheet width along the X-axis direction. To be strict, a nozzle row 77 extends in a direction intersecting both the X-axis direction and the Y-axis direction. The nozzle row 77 is used as a nozzle row configured to eject the disinfecting liquid. In other words, the nozzle rows 77 form a second liquid ejecting unit configured to eject the disinfectant liquid.

As described above, in the sheet transport direction, the downstream liquid ejecting head 76 configured to eject the disinfecting liquid is positioned downstream of the upper liquid ejecting head 73 in the +Y direction, or in the sheet transport direction, and thus a configuration can be obtained to eject the disinfecting liquid after the recording liquid is ejected.

Figure 6:
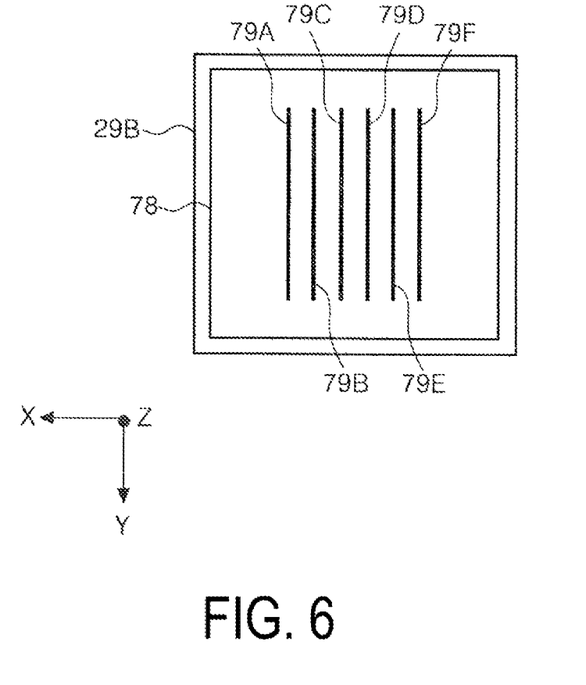
FIG. 6 is a diagram illustrating yet another embodiment of nozzle rows provided in a liquid ejecting head.

Also, the liquid ejecting head can be configured as illustrated in FIG. 6. A recording section 29B illustrated in FIG. 6 is a variation of the recording section 29 described above, and is an example of a head unit. The recording section 29B includes a liquid ejecting head 78 and the liquid ejecting head 78 includes a nozzle rows 79A, 79B, 79C, 79D, 79E, and 79F extending in the Y-axis direction. The recording section 29B is provided to be movable in the X-axis direction, or the sheet width direction, unlike the recording units 29 and 29A described above. In other words, the liquid ejecting head 78 is configured as a liquid ejecting head configured to eject ink while moving in the sheet width direction.

Note that the liquid ejecting head 78 is supplied with ink and disinfecting liquid by an ink tube (not illustrated) from a liquid accommodation section (not illustrated). The liquid accommodation section can be refilled with ink and disinfecting liquid. Note that, instead of the configuration described above, the recording section 29B may be configured to be removably provided with a cartridge containing ink and a cartridge containing disinfecting liquid.

Of the plurality of nozzle rows, the nozzle rows 79B, 79C, 79D, and 79E are used as ink ejecting nozzles. That is, the nozzle rows 79B, 79C, 79D, and 79E form a first liquid ejecting unit configured to eject recording ink. The ink ejected from the nozzle rows 79B, 79C, 79D, and 79E is, as an example, pigment ink of cyan (C), magenta (M), yellow (Y), and black (K), respectively. However, the ink is not limited to pigment ink and may be dye ink.

The nozzle rows 79A and 79F are then used as nozzles configured to eject the disinfecting liquid. In other words, the nozzle rows 79A and 79F form a second liquid ejecting unit configured to eject the disinfectant liquid.

Here, the nozzle row 79F configured to eject the disinfecting liquid is positioned, with a first direction being +X direction that is a moving direction when the recording section 29B moves, in a second direction, or −X direction, opposite to the first direction with respect to the nozzle rows 79B, 79C, 79D, and 79E.

Also, the nozzle row 79A configured to eject the disinfecting liquid is positioned, with a first direction being −X direction that is a moving direction when the recording section 29B moves, in a second direction, or +X direction, opposite to the first direction with respect to the nozzle rows 79B, 79C, 79D, and 79E.

Such a configuration enables a configuration to eject the disinfecting liquid after the ink is ejected to be obtained.

Note that, although all of the nozzle rows are provided in the identical liquid ejecting head 78 in the embodiment, the nozzle rows 79B, 79C, 79D, and 79E configured to eject ink and the nozzle rows 79A and 79F configured to eject the disinfecting liquid may be provided in separate liquid ejecting heads.

Next, suppression of curl of the medium using the disinfecting liquid will be described. When a difference is increased between total volume of liquid ejected onto a first surface of the medium and total volume of liquid ejected onto a second surface opposite to the first surface, there is a risk that curl is generated in the medium and alignment of the media output is degraded. In view of such a problem, the control unit 27 can perform control illustrated in FIG. 10.

Figure 10:
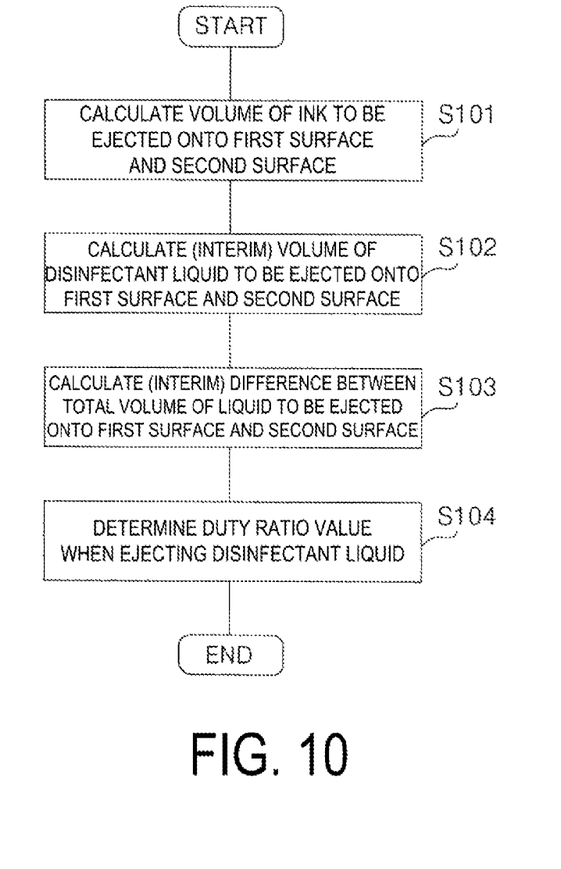
FIG. 10 is a flowchart illustrating a flow of determining of volume of disinfecting liquid ejected when recording is performed on both surfaces of a recording sheet.

In FIG. 10, the control unit 27 calculates, in response to receiving a printing start command, volume of ink to be ejected on each of the first surface and the second surface (step S101). Then, volume of disinfecting liquid to be ejected on each of the first surface and the second surface is calculated as an interim value (step S102). Here, a standard value is set for a duty ratio value when ejecting the disinfecting liquid, and in step S102, the volume of disinfecting liquid to be ejected on each of the first surface and the second surface is calculated based on the standard value. Note that the duty ratio value refers to volume of disinfecting liquid to be ejected per unit area. Hereinafter, the standard value of the duty ratio value is referred to as a standard duty ratio value.

The volume of disinfecting liquid to be ejected on each of the first surface and the second surface is calculated based on the disinfecting liquid ejecting region described with reference to FIGS. 7, 8, and 9. Here, whether either the disinfecting liquid ejecting region of FIG. 7, 8, or 9 is employed may be determined based on user setting or may be determined by the controller 27. This will be described later.

Next, the control unit 27 calculates a difference between the first surface and the second surface as the interim value for total volume of liquid obtained by adding the volume of ink to be ejected and the interim value of the volume of disinfecting liquid to be ejected (step S103). Next, the control unit 27 determines the duty ratio value which is used when ejecting the disinfecting liquid (step S104).

In step S104, the control unit 27 determines whether the interim value calculated at step S103, or the difference between total volume of liquid to be ejected onto first surface and second surface, is less than a predetermined threshold value, and if so, ejects the disinfecting liquid based on the standard duty ratio value. When the difference between total volume of liquid to be ejected onto first surface and second surface is equal to or greater than the predetermined threshold value, the duty ratio value when ejecting the disinfecting liquid is changed from the standard duty ratio value such that the difference is less than the threshold value. Then, the disinfection liquid is ejected based on the determined duty ratio value of the disinfecting liquid.

In this manner, the control unit 27 ejects the disinfecting liquid to reduce the difference between total volume of liquid to be ejected onto the first surface and total volume of liquid to be ejected onto the second surface on the medium, and thus curl generated in the medium can be suppressed and degradation in alignment of the media output can be suppressed.

The liquid ejecting device 1 also includes a drying section 50 configured to perform drying processing on the medium in the post-processing unit 5 downstream of the recording section 29. This can suppress degradation in alignment of the medium output with insufficiently dried condition, and can suppress transferring of the liquid between the media.

Note that in the calculation of the volume of disinfecting liquid ejected in step S102, whether either the disinfecting liquid ejecting region of FIG. 7, 8, or 9 is employed may be determined based on the user setting or may be determined by the controller 27 as described above.

For example, in case where the region is determined based on the user setting, a user can select either "prioritize disinfection", "prioritize image quality", or "four sides only" for the degree of disinfection via the operation section 28 (see FIG. 1), and when "prioritize disinfection" is selected, the disinfecting liquid ejecting region 102A described with reference to FIG. 7 is employed, when "prioritize image quality" is selected, the disinfecting liquid ejecting region 102B described with reference to FIG. 8 is employed, and when "four sides only" is selected, the disinfecting liquid ejecting region 102C described with reference to FIG. 9 is employed. Note that, of course, "no disinfection" in which ejection of the disinfecting liquid is not performed at all may be configured to be selectable.

In case where the control unit 27 determines the disinfecting liquid ejecting region, for example, when the print quality is specified as "fine", the disinfecting liquid ejecting region 102B described with reference to FIG. 8 or the disinfecting liquid ejecting region 102C described with reference to FIG. 9 is employed, and when the print quality is specified as "standard", the disinfecting liquid ejecting region 102A described with reference to FIG. 7 is employed. In this way, a good recording quality can be achieved by determining the disinfecting liquid ejecting region based on the printing quality.

Note that whether the selection of the disinfecting liquid ejecting region is determined based on the user setting or by the control unit 27, for a surface of the first and second surfaces onto which ink is not ejected, or a non-printing surface, the disinfecting liquid can be ejected throughout the non-printing surface, or the disinfecting liquid ejecting region 102C illustrated in FIG. 9 can be employed. Of course, the user may be allowed to set such that the disinfecting liquid is not ejected onto such a non-printing surface.

Figure 11:
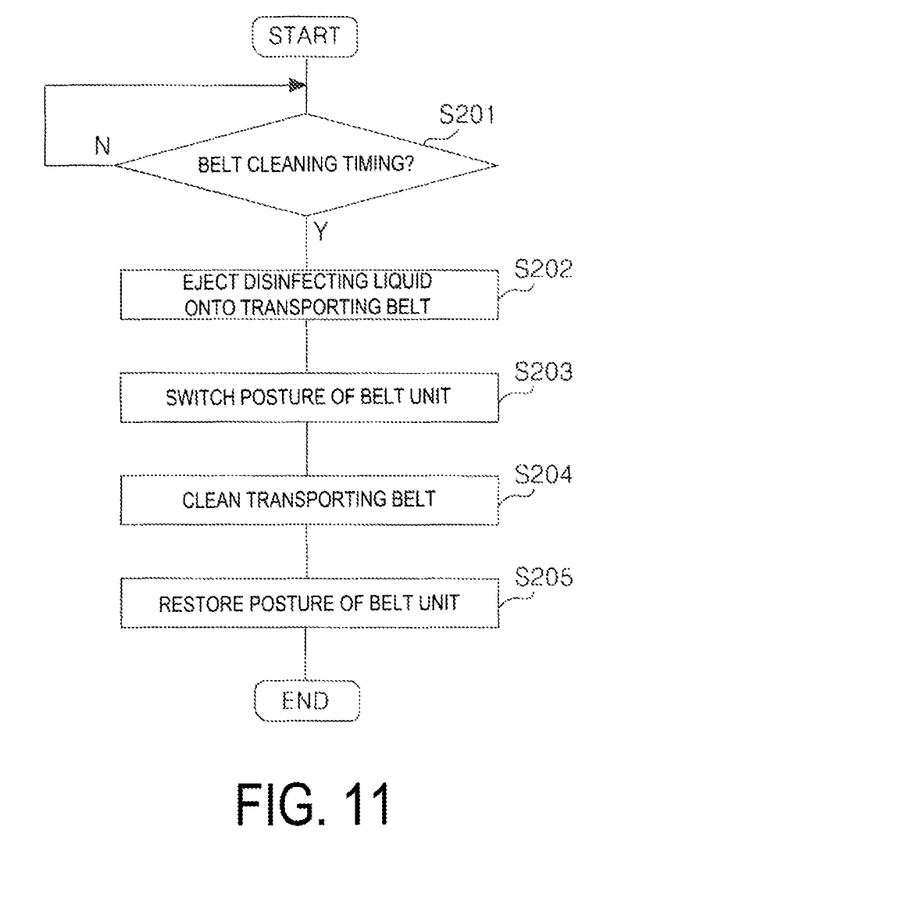
FIG. 11 is a flowchart illustrating a flow of cleaning mode to clean a transporting belt.

Referring now to FIG. 11, cleaning of the transporting belt 18c (see FIG. 3) will be described. The control unit 27 executes a cleaning mode in which cleaning of the transporting belt 18c is performed at a predetermined timing. The predetermined timing includes, for example, after a printing job is completed, a case where cumulative printed sheets has reached a predetermined number of sheets after executing the previous cleaning mode, or the like.

In FIG. 11, when the control unit 27 determines that it is the timing of cleaning the belt (step S201), the control unit 27 ejects the disinfecting liquid onto the transporting belt 18c (step S202). Note that ejection of the disinfecting liquid onto the transporting belt 18c in step S202 is performed while rotating the transporting belt 18c. As a result, the disinfecting liquid is ejected throughout the transporting belt 18c.

Next, a posture of the belt unit 18 is switched from a posture indicated by the two-dot chain line to a posture indicated by the solid line in FIG. 3 (step S203). Then, the transporting belt 18c is cleaned by the cleaning sheet 22 of the cleaning unit 20 while rotating the transporting belt 18c (step S204). Then, the posture of the belt unit 18 is returned to the posture indicated by the two-dot chain line from the posture indicated by the solid line in FIG. 3 (step S205).

Here, while the ink adhered to the transporting belt 18c can be wiped off by the cleaning sheet 22, cleaning effect on a particulate matter such as paper dust is weak. When particulate matter such as a paper dust is left on the transporting belt 18c, there is a risk that adsorption between the medium and the transporting belt 18c is degraded the next time the medium is transported and transport accuracy is degraded.

However, as described above, the control unit 27 includes a cleaning mode in which cleaning of the transporting belt 18c is performed by the cleaning sheet 22 after the disinfecting liquid is ejected onto the transporting belt 18c, and thus particulate matter such as paper dust adhered to the transporting belt 18c can be removed by the cleaning sheet 22.

Note that the present disclosure is not intended to be limited to the aforementioned embodiments, and many variations are possible within the scope of the present disclosure as described in the appended claims. It goes without saying that such variations also fall within the scope of the present disclosure.

For example, in the example described above, disinfecting liquid is ejected when ink is ejected, however, a mode may be provided in which the disinfecting liquid is ejected to one surface or both surfaces of the medium without ejecting ink to perform only disinfection processing of the medium without ejecting ink.

What is claimed is:

1. A liquid ejecting device comprising:
   a first liquid ejecting unit configured to eject recording liquid onto a medium;
   a second liquid ejecting unit configured to eject disinfectant liquid onto the medium; and
   a control unit configured to control the first liquid ejecting unit and the second liquid ejecting unit, wherein
   the control unit is configured to cause the disinfectant liquid to eject on the medium avoiding a position at which the recording liquid ejects.

2. The liquid ejecting device according to claim 1, wherein
   the control unit is configured to cause the disinfectant liquid to eject at margins along edges on four sides of the medium.

3. The liquid ejecting device according to claim 1, wherein
   the second liquid ejecting unit is disposed downstream of the first liquid ejecting unit in a transport direction of the medium.

4. The liquid ejecting device according to claim 1, comprising a head unit that includes the first liquid ejecting unit and the second liquid ejecting unit and configured to move in a width direction that is a direction intersecting the transport direction of the medium, wherein
   provided that a first direction is a moving direction in which the head unit moves, the second liquid ejecting unit is positioned in a second direction opposite to the first direction with respect to the first liquid ejecting unit.

5. The liquid ejecting device according to claim 1, wherein
   the first liquid ejecting unit and the second liquid ejecting unit are provided in an identical liquid ejecting head.

6. The liquid ejecting device according to claim 1, comprising a medium inversion path configured to invert the medium after a first surface of the medium passes through a position facing the first liquid ejecting unit and a position facing the second liquid ejecting unit such that a second surface opposite to the first surface faces the first liquid ejecting unit and the second liquid ejecting unit, wherein
   the control unit is configured to adjust a volume of the disinfectant liquid ejected from the second liquid ejecting unit to reduce a difference between a total volume of liquid ejected onto the first surface and a total volume of liquid ejected onto the second surface.

7. The liquid ejecting device according to claim 1, comprising:
   a transporting belt configured to transport the medium, the transporting belt being provided at a position facing the first liquid ejecting unit; and
   a cleaning sheet configured to contact and clean the transporting belt, wherein
   the control unit includes a cleaning mode in which cleaning of the transporting belt is performed by the cleaning sheet after the disinfectant liquid is ejected from the second liquid ejecting unit onto the transporting belt.

8. A liquid ejecting system comprising:
   the liquid ejecting device according to claim 1; and
   a drying section configured to perform drying processing on the medium, the drying section being provided downstream of the first liquid ejecting unit and the second liquid ejecting unit in the transport path of the medium.

9. A liquid ejecting method for a liquid ejecting device, the liquid ejecting device comprising:
   a first liquid ejecting unit configured to eject recording liquid onto a medium; and
   a second liquid ejecting unit configured to eject disinfectant liquid onto the medium, wherein
   the method comprising:
   causing the disinfectant liquid to eject on the medium avoiding a position at which the recording liquid ejects.

* * * * *